(12) United States Patent
Gurley

(10) Patent No.: US 11,801,065 B2
(45) Date of Patent: Oct. 31, 2023

(54) CATHETER SYSTEMS, KITS, AND METHODS FOR GAINING ACCESS TO A VESSEL

(71) Applicant: Merit Medical Systems, Inc., South Jordan, UT (US)

(72) Inventor: John Gurley, Lexington, KY (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 17/089,551

(22) Filed: May 24, 2023

(65) Prior Publication Data
US 2021/0186535 A1 Jun. 24, 2021

Related U.S. Application Data

(62) Division of application No. 15/444,510, filed on Feb. 28, 2017, now Pat. No. 10,856,892.

(60) Provisional application No. 62/301,397, filed on Feb. 29, 2016.

(51) Int. Cl.
*A61B 17/22* (2006.01)
*A61M 25/00* (2006.01)
*A61B 90/00* (2016.01)

(52) U.S. Cl.
CPC .... *A61B 17/22* (2013.01); *A61B 2017/22094* (2013.01); *A61B 2090/3966* (2016.02); *A61M 2025/0095* (2013.01)

(58) Field of Classification Search
CPC .......................... A61B 17/22; A61B 2090/3966
See application file for complete search history.

(56) References Cited

U.S. PATENT DOCUMENTS

| | | | |
|---|---|---|---|
| 4,559,039 A | 12/1985 | Ash et al. |
| 5,152,749 A | 10/1992 | Giesy et al. |
| 5,800,378 A | 9/1998 | Edwards et al. |
| 5,851,195 A | 12/1998 | Gill |
| 5,925,016 A | 7/1999 | Chornenky et al. |
| 6,190,353 B1 | 2/2001 | Makower et al. |
| 6,217,527 B1 | 4/2001 | Selmon et al. |
| 6,283,951 B1 | 9/2001 | Flaherty et al. |
| 6,475,226 B1 | 11/2002 | Belef et al. |
| 6,655,386 B1 | 12/2003 | Makower et al. |
| 6,662,036 B2 | 12/2003 | Cosman |
| 6,685,722 B1 | 2/2004 | Rosenbluth et al. |

(Continued)

FOREIGN PATENT DOCUMENTS

| | | |
|---|---|---|
| JP | 2002-516696 | 6/2002 |
| WO | WO 00/18323 | 4/2000 |

(Continued)

OTHER PUBLICATIONS

International Preliminary Report on Patentability issued in PCT/US2013/024738, dated Feb. 18, 2014.

(Continued)

*Primary Examiner* — Tasnim Mehjabin Ahmed
(74) *Attorney, Agent, or Firm* — Dorsey & Whitney LLP

(57) ABSTRACT

Some of the present methods include, and some embodiments of the present systems are configured for gaining access to a patient's vessel by way of the vessel (i.e. from the inside out). Some embodiments facilitate gaining access to an occluded vessel, where part of the access path is through the occlusion.

13 Claims, 19 Drawing Sheets

(56) References Cited

U.S. PATENT DOCUMENTS

| | | | |
|---|---|---|---|
| 6,726,677 | B1 | 4/2004 | Flaherty et al. |
| 7,059,330 | B1 | 6/2006 | Makower et al. |
| 7,134,438 | B2 | 11/2006 | Makower et al. |
| 7,179,220 | B2 | 2/2007 | Kukuk |
| 7,635,353 | B2 | 12/2009 | Gurusamy et al. |
| 7,678,081 | B2 | 3/2010 | Whiting et al. |
| 8,029,470 | B2 | 10/2011 | Whiting et al. |
| 8,337,518 | B2 | 12/2012 | Nance et al. |
| 8,357,193 | B2 | 1/2013 | Phan et al. |
| 8,500,768 | B2 | 8/2013 | Cohen |
| 8,568,435 | B2 | 10/2013 | Pillai et al. |
| 8,771,287 | B2 | 7/2014 | Wynberg |
| 8,795,310 | B2 | 8/2014 | Fung et al. |
| 8,814,873 | B2 | 8/2014 | Schaller et al. |
| 2002/0022857 | A1 | 2/2002 | Goldsteen et al. |
| 2003/0191449 | A1 | 10/2003 | Nash et al. |
| 2003/0220698 | A1 | 11/2003 | Mears et al. |
| 2004/0165966 | A1 | 8/2004 | Aukzemas et al. |
| 2004/0181150 | A1 | 9/2004 | Evans et al. |
| 2004/0199177 | A1 | 10/2004 | Kim |
| 2005/0021002 | A1 | 1/2005 | Deckman et al. |
| 2005/0125002 | A1 | 6/2005 | Baran et al. |
| 2005/0209579 | A1 | 9/2005 | Yacoubian et al. |
| 2005/0288695 | A1 | 12/2005 | Jenson et al. |
| 2006/0106288 | A1 | 5/2006 | Roth et al. |
| 2006/0173269 | A1 | 8/2006 | Glossop |
| 2006/0276749 | A1* | 12/2006 | Selmon .................. A61B 6/12 604/164.01 |
| 2007/0135803 | A1 | 6/2007 | Belson |
| 2007/0166345 | A1 | 7/2007 | Pavonik et al. |
| 2007/0203517 | A1 | 8/2007 | Williams et al. |
| 2008/0230070 | A1 | 9/2008 | Gregorian |
| 2009/0005755 | A1 | 1/2009 | Keith et al. |
| 2009/0240122 | A1 | 9/2009 | Avitsian |
| 2009/0281379 | A1 | 11/2009 | Binmoeller et al. |
| 2010/0056862 | A1 | 3/2010 | Bakos |
| 2010/0249491 | A1 | 9/2010 | Farnan et al. |
| 2012/0136247 | A1 | 5/2012 | Pillai |
| 2012/0136320 | A1 | 5/2012 | Pillai et al. |
| 2012/0136366 | A1 | 5/2012 | Pillai |
| 2012/0239069 | A1 | 9/2012 | Benscoter et al. |
| 2013/0035628 | A1* | 2/2013 | Garrison ................ A61B 17/22 604/9 |
| 2013/0197621 | A1 | 8/2013 | Ryan et al. |
| 2013/0317528 | A1 | 11/2013 | Anderson et al. |
| 2014/0142418 | A1* | 5/2014 | Gurley .................. A61M 25/09 600/424 |
| 2015/0182727 | A1 | 7/2015 | Gurley et al. |

FOREIGN PATENT DOCUMENTS

| | | |
|---|---|---|
| WO | WO 2006/105244 | 10/2006 |
| WO | WO 2008/070262 | 6/2008 |
| WO | WO 2009/100129 | 8/2009 |
| WO | WO 2011/068540 | 6/2011 |
| WO | WO 2013/181397 | 12/2013 |

OTHER PUBLICATIONS

International Search Report and Written Opinion issued in PCT/US2010/003078, dated Feb. 2, 2011.
International Search Report and Written Opinion issued in PCT/US2013/024738, dated Apr. 30, 2013.
Office Action issued in Chinese Patent Application No. 2013800090393, dated Jun. 20, 2016. (English Translation Provided).
Office Action Issued in Corresponding European Patent Application No. 17759351.4, dated Sep. 24, 2019.
Office Action issued in Japanese Patent Application No. 2014-556613, dated Sep. 9, 2016. (English Translation Provided).
Office Action issued in U.S. Appl. No. 12/958,702, dated Dec. 28, 2012.
Office Action issued in U.S. Appl. No. 13/680,327, dated Jan. 29, 2014.
Office Action issued in U.S. Appl. No. 13/680,327, dated May 29, 2014.
Office Action issued in U.S. Appl. No. 13/680,327, dated Nov. 7, 2014.
Office Communication Issued in European Patent Application No. 13747174.4, dated Jul. 13, 2016.
Supplementary European Search Report issued in European Patent Application No. 17759351, dated Oct. 26, 2018.

* cited by examiner

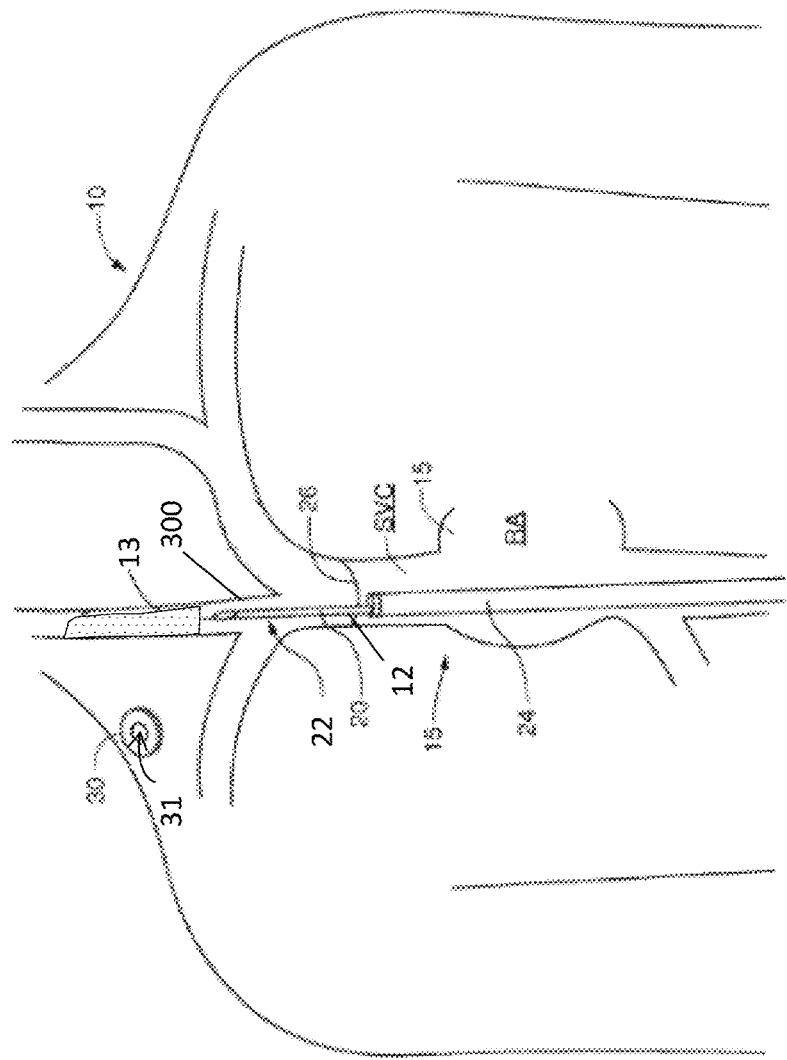

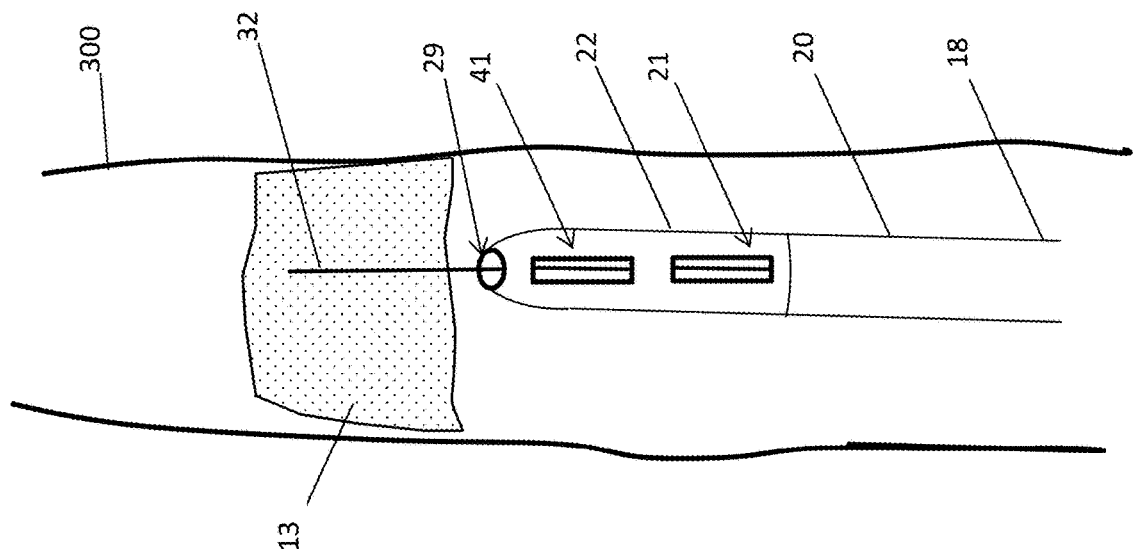

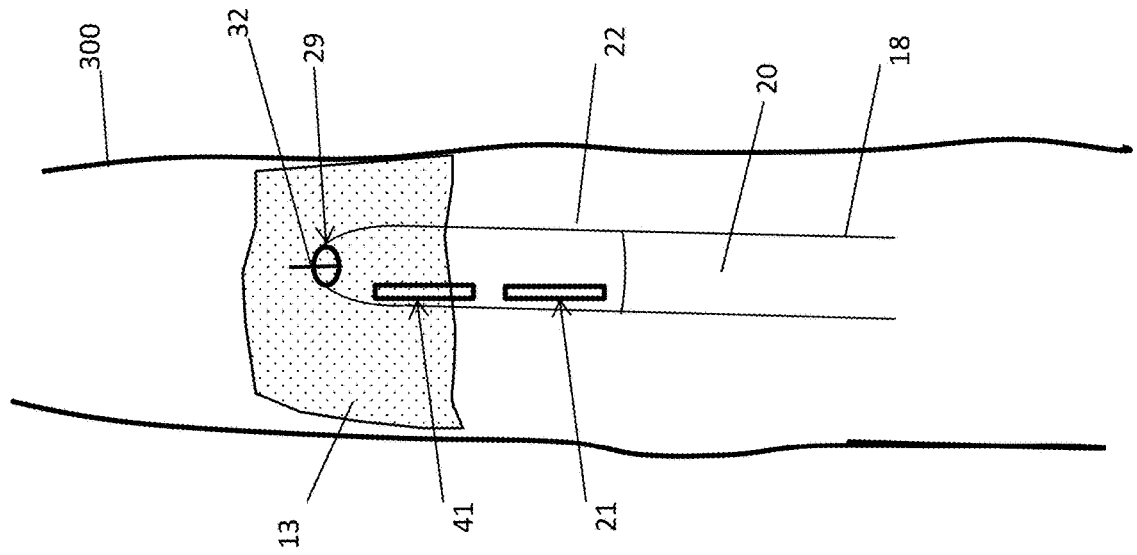

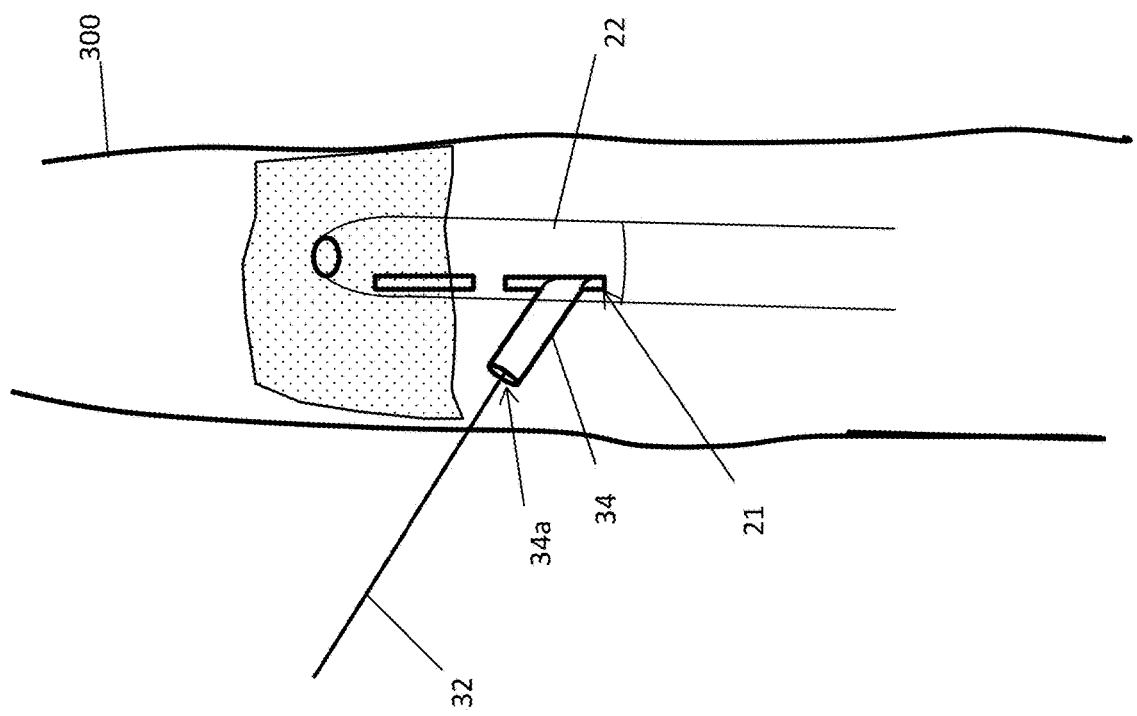

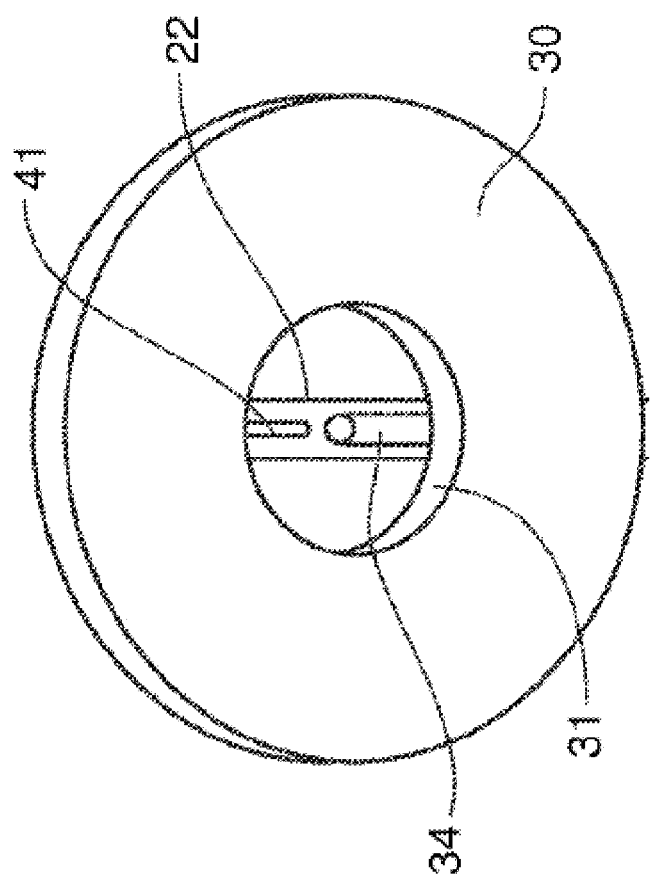

CATHETER SYSTEMS, KITS, AND METHODS FOR GAINING ACCESS TO A VESSEL

CROSS-REFERENCE TO RELATED APPLICATIONS

This application is a divisional of U.S. application Ser. No. 15/444,510, filed Feb. 28, 2017, which claims priority to U.S. Provisional Application No. 62/301,397 filed Feb. 29, 2016, the entire contents of each of which are specifically incorporated herein by reference without disclaimer.

BACKGROUND

1. Field of Invention

The present invention relates generally to catheter systems, kits, and methods of using the catheter systems and kits useful for gaining access to a vessel by way of the vessel.

2. Description of Related Art

Access to a patient's vascular system, e.g., the central venous or arterial system, of a patient can be necessary to carry out many lifesaving medical procedures. For example, the usual method of gaining access to the venous system in the area of the neck is to directly puncture a major vein in the neck with a large gauge needle through which a guide wire is placed. This approach is described as going from the outside (skin) to inside the vein/vessel. The guide wire supports the remainder of the intervention at the site that usually results in the placement of an introducer sheath or the like. A problem can arise however when a major vein is blocked with a clot or fibrous occlusion. Similarly, a problem can also arise when an artery is blocked with a clot or fibrous occlusion.

SUMMARY

Embodiments of the present disclosure facilitate gaining access to a patient's vessel by way of the patient's vasculature (i.e. from the inside out). Some embodiments facilitate gaining access to an occluded vessel, where part of the access path is through the occlusion. The occlusion is first penetrated by a needle wire and then by a larger diameter catheter that then directs a second catheter along a path that is at an angle to the longitudinal axis of the larger diameter catheter (e.g., projection angle). In some embodiments, the occluded vessel is in the upper chest and/or neck (e.g., at a location near the clavicle).

One embodiment of the present disclosure is a method for providing access to a central venous system of a patient. Such methods can comprise: applying a radiopaque target having a radiopaque area and a radiolucent area to the skin of the patient so that the radiolucent area defines an exit point on the skin of the patient introducing a catheter and a projection angle catheter into the patient in an area remote from the exit point, wherein the projection angle catheter is configured to extend out a side aperture of a distal tip of the catheter at a projection angle, and a needle wire is configured to extend through the projection angle catheter, wherein the catheter has a aperture at a distal end of the distal tip configured such that the needle wire can extend through the aperture advancing the needle wire through the distal end aperture of the catheter to a desired location in the central venous system; advancing the catheter to position said distal tip in a desired tip location in the central venous system; viewing the catheter and said distal tip under fluoroscopy through the radiolucent area of the radiopaque target; rotating the catheter so that the side aperture and therefore the projection angle plane is aligned with the radiolucent area of the radiopaque target; adjusting the projection angle catheter so that the projection angle is aimed at the radiolucent area of the radiopaque target; and advancing the needle wire through the projection angle catheter, such that the distal end of the needle wire advances at an angle relative to the catheter and penetrates the skin of the patient adjacent the radiolucent area of the radiopaque target thereby providing a distal end of the needle wire exterior to the skin.

Another embodiment for providing access to a central venous system of a patient can comprise: introducing a catheter into the patient, wherein the catheter has a projection angle catheter configured to extend out a side aperture of a distal tip of the catheter at a projection angle, and a needle wire configured to extend through the projection angle catheter, wherein the catheter has an aperture at a distal end of the distal tip configured such that the needle wire can extend through the aperture in a direction substantially parallel with a longitudinal axis of the catheter, wherein the projection angle is angled with respect to the longitudinal axis; advancing the needle wire through the distal end aperture of the catheter and into a vessel occlusion; advancing the catheter to position said distal tip in a desired tip location; retracting the needle wire into the catheter and the projection angle catheter; advancing the projection angle catheter so that the catheter extends through the side aperture; and advancing the needle wire through the projection angle catheter and through the skin of the patient, thereby providing a distal end of the needle wire exterior to the skin.

Another embodiment of the present disclosure can comprise a catheter system. Such systems can comprise: a first catheter that can comprise a shaft comprising a proximal end and a distal end extending along a longitudinal axis and defining a lumen extending therebetween; a distal tip disposed at the distal end of the shaft and defining a lumen extending along a longitudinal axis and in fluid communication with the shaft lumen and comprising a distal end, wherein the distal tip comprises a side aperture in fluid communication with the shaft lumen and an aperture at the distal end in fluid communication with the shaft lumen; a second catheter having a portion configured to extend through the shaft lumen and the side aperture, the second catheter comprising a proximal end and a distal end and defining a lumen along a longitudinal axis between the proximal end and the distal end, wherein a portion of the second catheter is curved along the longitudinal axis and the curved portion is closer to the distal end than the proximal end, wherein the first catheter and the second catheter are configured such that the distal end of the second catheter passes through the side aperture of the first catheter when advanced through the first catheter; and a needle wire configured to extend through the second catheter lumen and to extend through the distal end exit aperture of the first catheter in a direction substantially parallel with the longitudinal axis of the shaft, the needle wire having a sharp dissection tip, wherein the needle wire is configured such that it can penetrate a muscle tissue without deflection.

The term "coupled" is defined as connected, although not necessarily directly, and not necessarily mechanically; two items that are "coupled" can be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" can be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment can be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number can be used to indicate a similar feature or a feature with similar functionality, as can non-identical reference numbers.

FIG. 1A illustrates a needle wire extending from a distal end, and FIG. 1B illustrates the needle wire and a catheter extending from a side aperture.

FIG. 3A is a cross-sectional, schematic view of a patient with a vessel occlusion involving a vessel in the upper chest region above the level of the superior vena cava (SVC) and the right atrium. A portion of a catheter system embodiment is shown extending through the vessel.

FIGS. 3B-3H are schematic illustrations of a series of process steps of an embodiment of using a catheter system, the illustration showing a vessel with a vessel occlusion and the distal portion of a catheter system embodiment. FIG. 3A is similar to FIG. 3B yet provides a wider perspective of a catheter system extending through the vessel, proximal an occlusion.

FIG. 3I is a cross-sectional, schematic view of a patient with a vessel occlusion involving a vessel in the upper chest region above the level of the superior vena cava (SVC) and the right atrium, and a portion of a catheter system embodiment extending through the vessel and into an occlusion.

FIG. 4 is a schematic of a radiopaque target embodiment aligned with a distal tip embodiment. Some or all of the elements may be viewable with radiographic imaging.

DETAILED DESCRIPTION

Figure 1A:
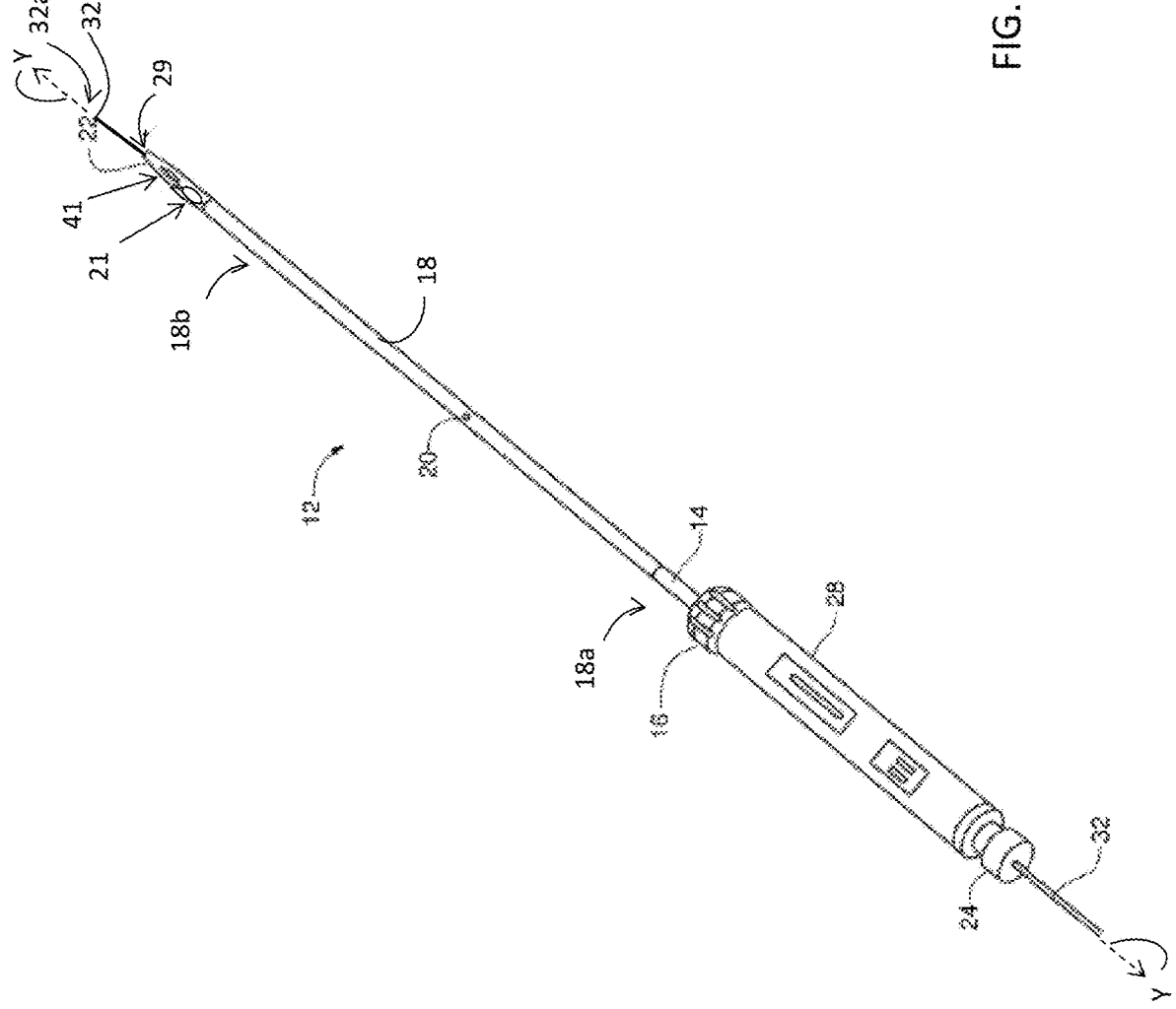
FIGS. 1A and 1B are schematic views of an embodiment of a catheter system.
Figure 1B:
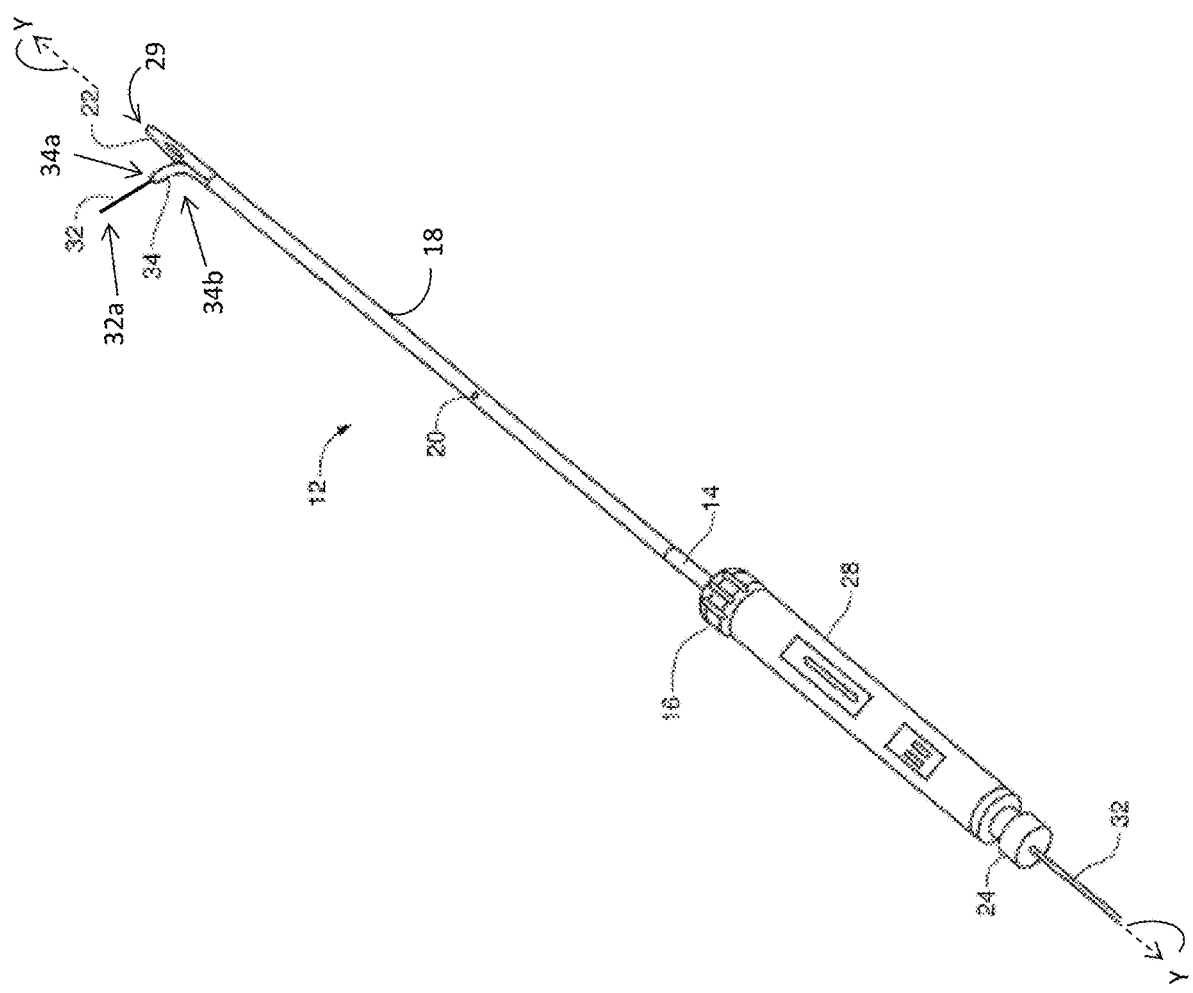

FIGS. 1A to 1D illustrate one embodiment of a catheter system 12. In FIGS. 1A and 1B, system 12 is shown as a schematic view with components of the system in different positions. Catheter system 12 comprises a catheter 20, a catheter 34 configured to extend at least partially through catheter 20, and a needle wire 32 configured to extend through catheter 34. Catheter 20 comprises a shaft 18 having a proximal end 18a and a distal end 18b. Shaft 18 at proximal end 18a is coupled to a handle 28 through an optional resilient member 14 that defines a lumen in communication with the lumen of catheter 20. Distal tip 22 is disposed at the distal end 18b of shaft 18.

Figure 1C:
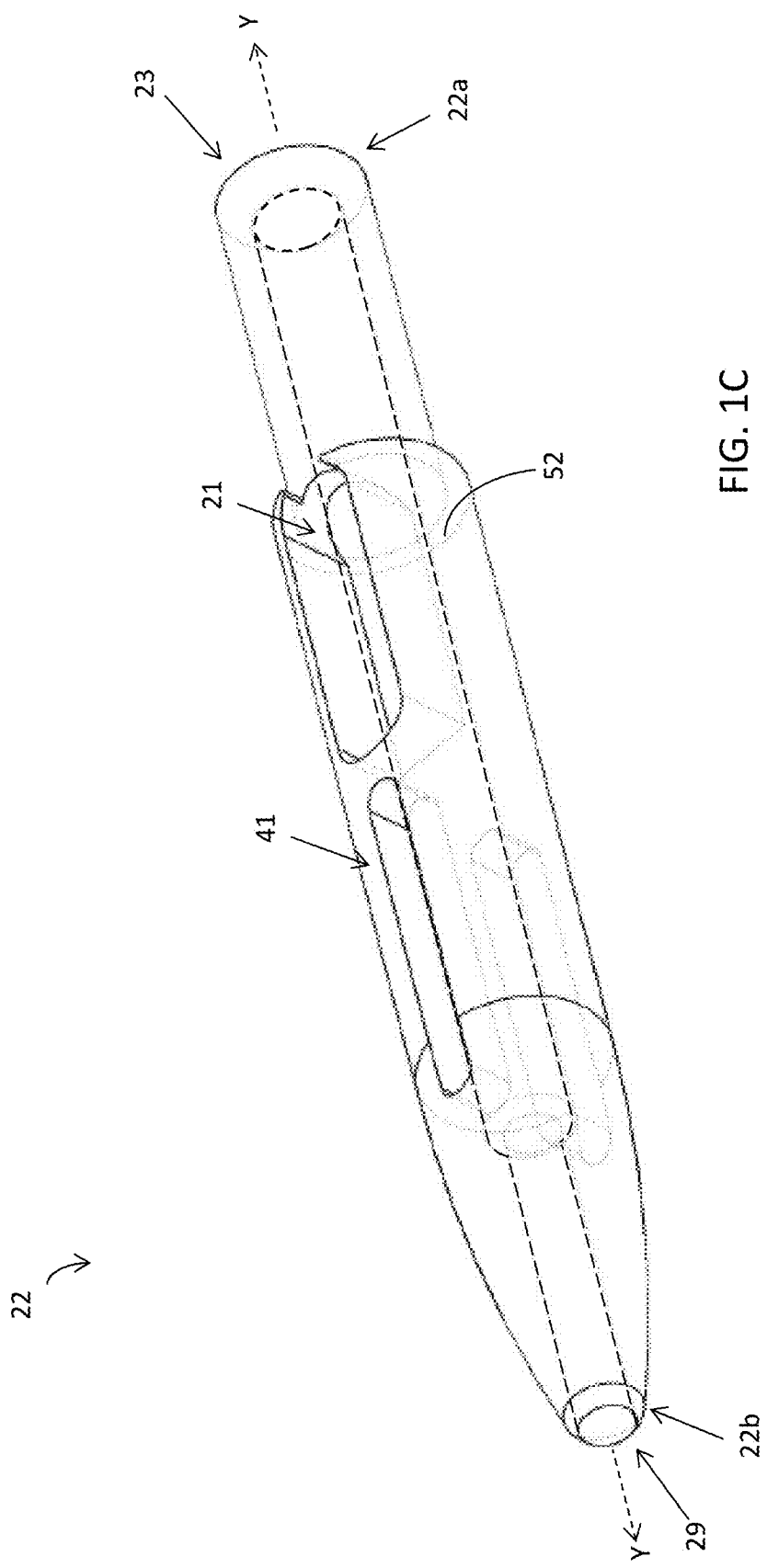
FIG. 1C is an isolated, magnified, top perspective view of the distal tip of the embodiment shown in FIGS. 1A and 1B.
Figure 1D:
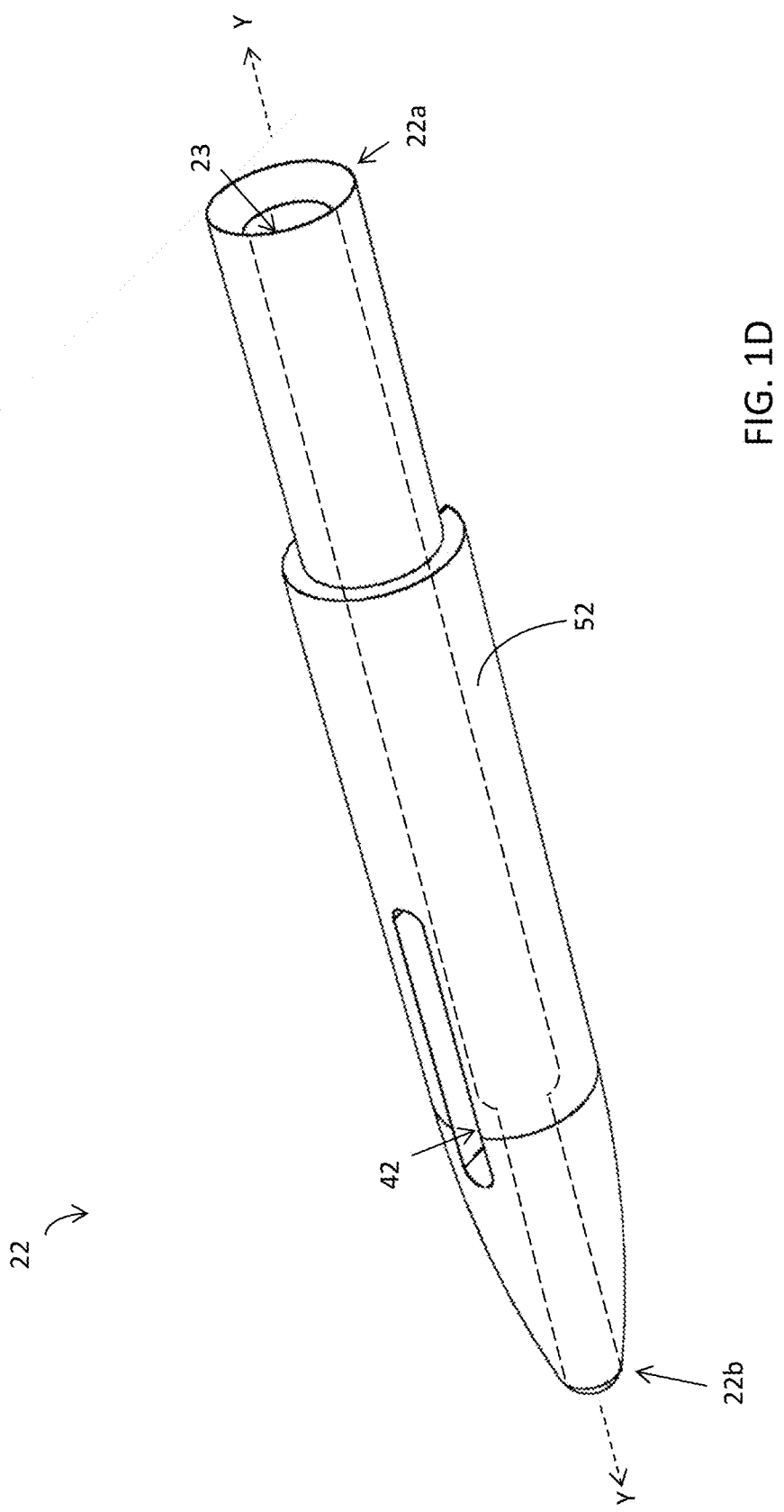
FIG. 1D is an isolated, magnified, bottom perspective view of the distal tip of the embodiment shown in FIG. 1C.

FIGS. 1C and 1D show a magnified top, perspective view and bottom, perspective view of a distal tip 22 of catheter 20. Distal tip 22 defines a lumen 23 that is in fluid communication with the lumen of shaft 18. Distal tip 22 comprises a side aperture 21 disposed between a proximal end 22a and a distal end 22b of the distal tip. Distal tip 22 also comprises an aperture 29 at distal end 22b. Both side aperture 21 and aperture 29 are in fluid communication with lumen 23 of distal tip 22. Distal tip 22 and needle wire 32 are configured such that the distal end of needle wire can extend through lumen 23 and distal end aperture 29 (e.g., a transverse dimension of the aperture and conduit is greater than a maximum transverse dimension of the needle wire). Side aperture 21 and catheter 34 are configured such that catheter 34 can extend through the side aperture (e.g., cross-sectional dimension of the aperture is greater than a maximum transverse, cross-sectional dimension of catheter 34) when entering lumen 23 through proximal end 22a. In the embodiment shown, the transverse cross-sectional area of lumen 23 is greater at the proximal end 22a than the distal end 22b since the distal end 22b only needs to accommodate needle wire 32.

Distal tip 22 can also comprise side aperture 41 (FIG. 1C) and/or side aperture 42 (FIG. 1D). Side apertures 41 and/or 42 can be disposed between proximal end 22a and distal end 22b of distal tip 22 and can be in fluid communication with lumen 23 of distal tip 22. Distal tip 22 can comprise a radiopaque material that defines at least a portion of side aperture 41 and/or side aperture 42. Side aperture 41 and/or side aperture 42 can be used as reference guide during the circumferential alignment of catheter 20. The visibility of side aperture 41 and/or 42 will vary with the axial rotation distal tip 22. When viewing a real-time radiographic image of distal tip 22, side apertures 41 and/or 42 will appear widest and/or brightest when the plane of a radiographic detector is aligned with (e.g., in the same plane as) apertures 41 and/or 42. The aiming and alignment of the distal tip 22 will be described in further detail below. This angle can be used to select the projection angle at which catheter 34 extends from side aperture 21 and/or define the exit path of a needle wire 32 advancing from catheter 34. When the projection angle of catheter 34 substantially corresponds to the angle of the detector plane, the exit path of needle wire 32 will intersect the desired exit site on the patient. In some embodiments, side aperture 21 can also be defined by a radiopaque material to facilitate the rotational alignment and angle setting process. Distal tip 22 can be coupled to or integral with shaft 18.

Catheter 34 is configured to extend through side aperture 21 at an angle relative to the longitudinal axis Y of catheter 20. The angle is defined by the section of catheter 34 extending through side aperture 21 and is referred to as the projection angle θ (see FIG. 3I). The projection angle θ corresponds to the angle of the exit path 38 of needle wire 32 relative to distal tip 22 (e.g., the angle of the tissue track). Catheter 34 and distal tip 22 can be configured such that the projection angle can be selectively adjusted. For example, catheter 34 can comprise a resilient section 34b near distal end 34a that is curved along the longitudinal axis of catheter 34 in a preformed shape. When disposed within catheter 20, curved section 34b is held in a less curved configuration by sidewall 52 of catheter 20. However, by advancing catheter 34 in a distal direction, distal end 34a becomes adjacent side aperture 21 and the constraint by sidewall 52 is reduced and the curved section 34b adopts a more curved or less constrained configuration. As distal end 34a progressively extends through side aperture 21, the projection angle θ increases. In this manner, catheter 34 moves through a range of projection angles θ as the length of catheter 34 extending from side aperture 21 is increased or decreased. In some embodiments, the length (dimension along longitudinal axis Y) of side aperture 21 can be such that the constraint on catheter 34 is sufficiently reduced and the distal end 34a is able to advance at an angle through side aperture 21 and not intersect (e.g., clear or not get hung on) sidewall 52.

In some embodiments, catheter 34 is configured not to rotate (e.g., spin) within the lumen of catheter 20. This restraint on rotational movement allows for the inner curved surface of curved section 34b to remain facing in the direction of side aperture 21. This can assist in the reliability of the exit of catheter 34 through the side aperture. One mechanism for restraining rotation within the lumen of catheter 20 is to have a channel longitudinally disposed in surface of catheter 34 that receives (e.g., interlocks with) a rigid protrusion that is disposed in handle 28 or on the luminal surface of catheter 20 such that longitudinal movement is not restrained by this mechanism, only rotational movement.

In some embodiments, particularly those that are used to penetrate an occlusion, catheter 20 can be configured to be sufficiently push-able (in a proximal-distal direction) and/or torque-able to allow distal tip 22 to be forced into a vessel occlusion (e.g., a thrombus). In some embodiments, catheter system 12 is configured such that the distal tip 22 can penetrate a vessel occlusion without deflection. In some embodiments, an appropriate value of bending stiffness can be between 30-60 (pounds force) times (inches squared) (e.g., about 30, 35, 40, 45, 50, 55, or 60 (pounds force) times (inches squared)). For example, a stainless steel tube with an inside diameter of 0.074 inches and outside diameter of 0.094 inches would be sufficient for this purpose. However it is understood that any variety of materials with various wall thicknesses can be pushed and/or torqued to force distal tip 22 into an occlusion. Other embodiments can comprise a polymeric tube. Such tubes may comprise higher stiffness braided or coiled materials like metals embedded in the polymer.

The magnitude of the forces required can also depend on the "sharpness" of the distal tip 22 and the overall diameter. In some embodiments, the tip can be blunted distal end or where the transverse cross-sectional area of the distal end 22b is at least 1.5× the area of the aperture 29. In other embodiments, the tip can have a distal end that tapers toward aperture 29 or where the transverse cross-sectional area of the distal end 22b is less than 1.5× the area of the aperture 29.

Needle wire 32 can be configured to penetrate a muscle tissue and/or thrombus at a distal end 32a without deflection. For example, needle wire 32 can comprise a trocar-type tip or sharp dissection tip at distal end 32a. Such tip can be blunted, flat and angled, conical, or pyramidal in shape. Needle wire 32 can also have a bending stiffness sufficient to penetrate a tissue without deflection. Suitable needle wire materials can include any medical grade material that can provide the material properties needed to perform the above function, e.g., steel, titanium (e.g., titanium alloy or nitinol), or the like.

In some embodiments, the needle wire 32 is made of nitinol with 55-57% nickel and 43-45% titanium. For example, nitinol can comprise the following composition (in wt %):

| Chemical Composition (reference ASTM F2063) | wt % |
| --- | --- |
| Nickel (nominal) | 55.96 |
| Titanium | 43.98 |
| Carbon | 0.025 |
| Cobalt | 0.00033 |
| Copper | 0.00038 |
| Chromium | 0.00024 |
| Hydrogen | 0.0001 |
| Iron | 0.0094 |
| Niobium | <0.00002 |
| Oxygen | 0.0288 |

In some embodiments, the diameter of needle wire 32 can be between 0.02 in. to 0.03 in., e.g., 0.020 in., 0.021 in., 0.022 in, 0.023 in., 0.024 in., 0.025 in., 0.026 in., 0.027 in., 0.028 in., 0.029 in., or 0.030 in.

In some embodiments, needle wire 32 can be a drawn filled tube wire comprising a radiopaque core. In some embodiments, the outer sheath is nitinol. In some embodiments, the core can be at least located on the distal end and not extending the entire length.

Figure 1E:
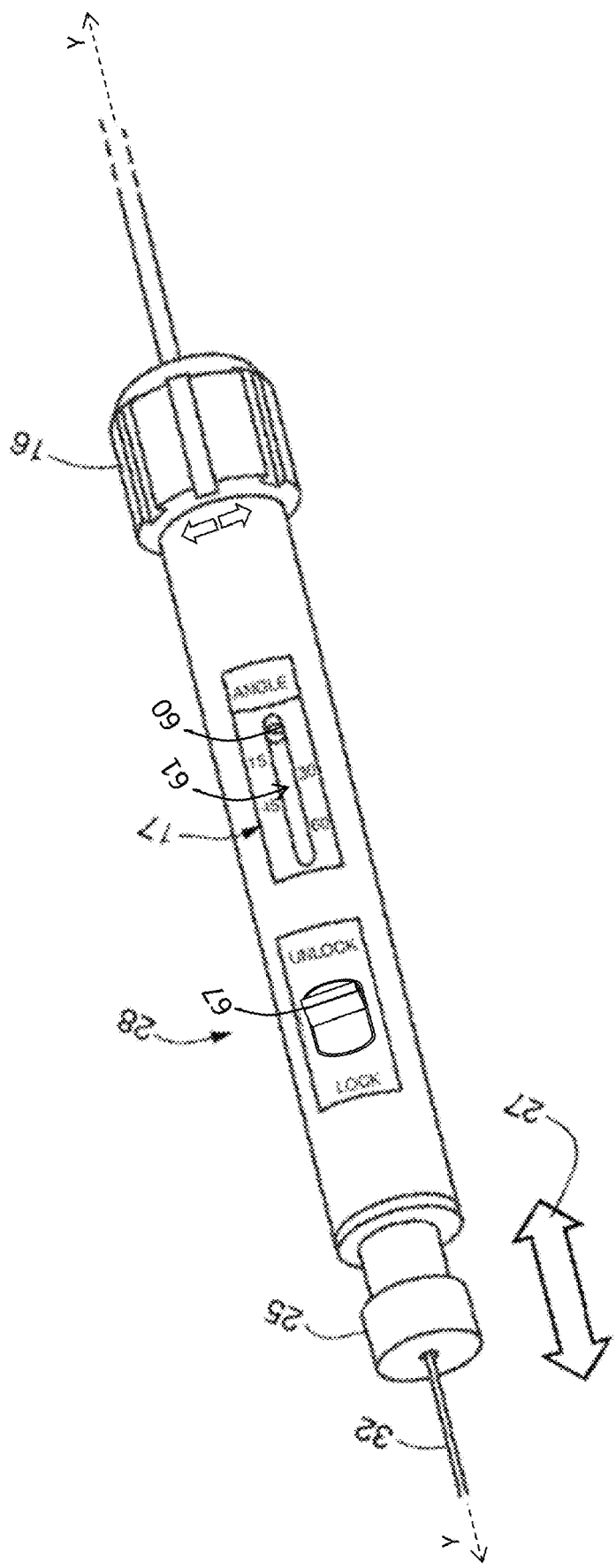
FIG. 1E is a schematic, perspective view of the handle shown in embodiment of FIG. 1A.
Figure 1F:
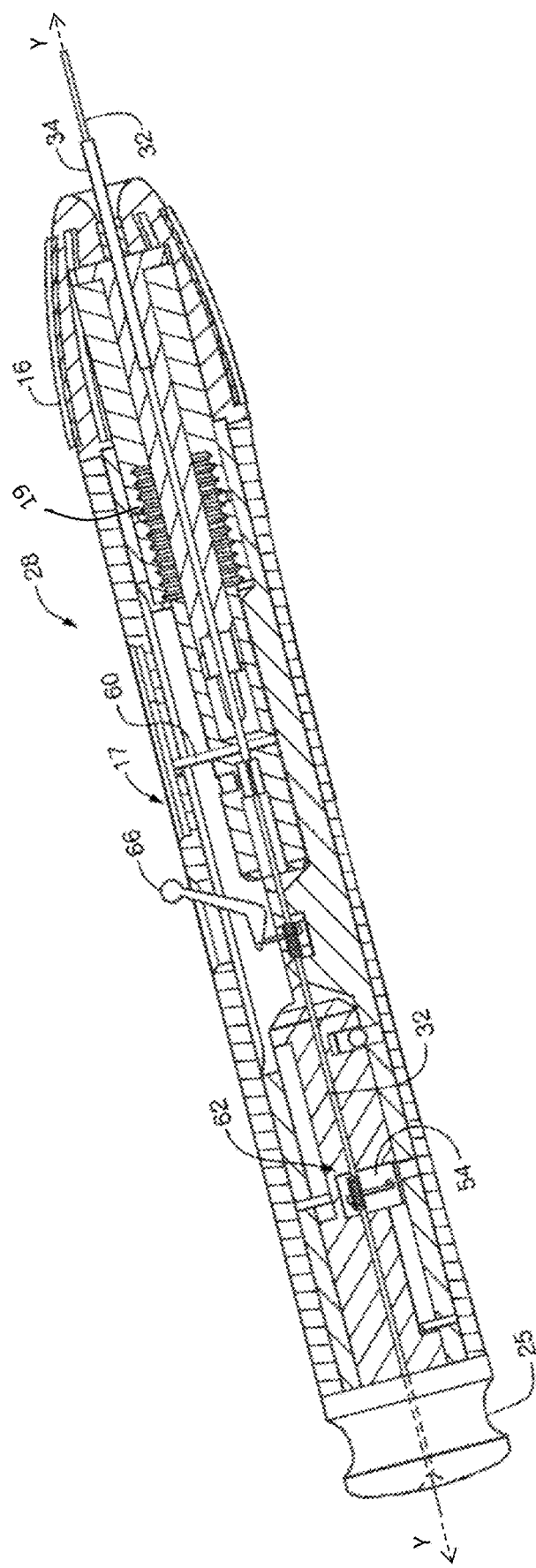
FIG. 1F is a schematic, cross-sectional view of the handle shown in FIG. 1E.

Catheter system 12 can further comprise handle 28. A magnified, isolated, and exterior view of handle 28 is provided in FIG. 1E and a cross-sectional view is provided in FIG. 1F. In embodiment shown, handle 28 is approximately cylindrical with a central axis Y. Handle 28 can be configured to axially rotate distal tip 22 of catheter 20, catheter 20, and/or catheter 34. In some embodiments, handle 28 is configured such that its axial rotation axially rotates catheter 20 and/or catheter 34. This motion facilitates the rotational alignment of distal tip 22 relative to a radiographic detector as described above.

Handle 28 can also be configured to advance catheter 34 through catheter 20 and out of side aperture 21. In the embodiment shown, rotary knob 16 is configured to turn in a clockwise and/or counter clockwise direction thereby advancing and/or retracting catheter 34. Handle 28 also comprises a gauge or scale 17 that indicates the projection angle θ of catheter 34. The position of catheter 34 and the projection angle θ is displayed on gauge or scale 17 in handle 28. Thus, knob 16 is configured to adjust the projection angle θ of catheter 34 and adjust the reading from the scale 17. For example, knob 16 can be configured such that its rotation turns a threaded body 19, whereby the threaded body's rotation advances or retracts catheter 34 depending upon direction of rotation. Knob 16 can also be configured such that its rotation translates post 60 within companion slot 61, whereby indicating the projection angle based upon the post's position relative to scale 17.

Handle 28 can also be configured to advance and/or retract needle wire 32 through catheter 34 and distal tip 22. For example, handle 28 can comprise a wire clamping and propelling mechanism located within the handle 28 that allows the user to advance the needle wire 32 out of the handle. Wire clamping and propelling mechanism can comprise a J-arm clamp 62 coupled to pommel 25. Pommel 25 is movable with a reciprocating motion (or piston-like motion), as indicated by motion arrow 27. Pommel 25 is coupled to J-arm clamp 62 that is configured to wedge against needle wire 32 as the pommel is advanced distally and to release the needle wire upon a return stroke of the pommel. J-arm clamp 62 is configured to remain stationary while the pommel moves during the return stroke. Pommel 25 and handle 28 are configured to support the wire 32 during the stroke so that needle wire 32 does not bend or kink. The stroke is relatively fixed so that a user may count the number of pommel strokes to have an estimate of how much needle wire 32 has been advanced. Retracting needle wire 32 can occur by proximally pulling the wire.

Handle 28 can also comprise a releasable locking mechanism 66 configured to fix the axial position of needle wire relative to handle 28 so the withdrawal of the handle also pulls the needle wire. When unlocked, needle wire 32 can move axially relative to handle 28 to facilitate the removal of catheters 20 and catheter 34 from body while the needle wire remains in place. Releasable locking mechanism 66 comprises a toggle switch 67 to alternate the mechanism between a lock and unlock position.

Figure 2A:
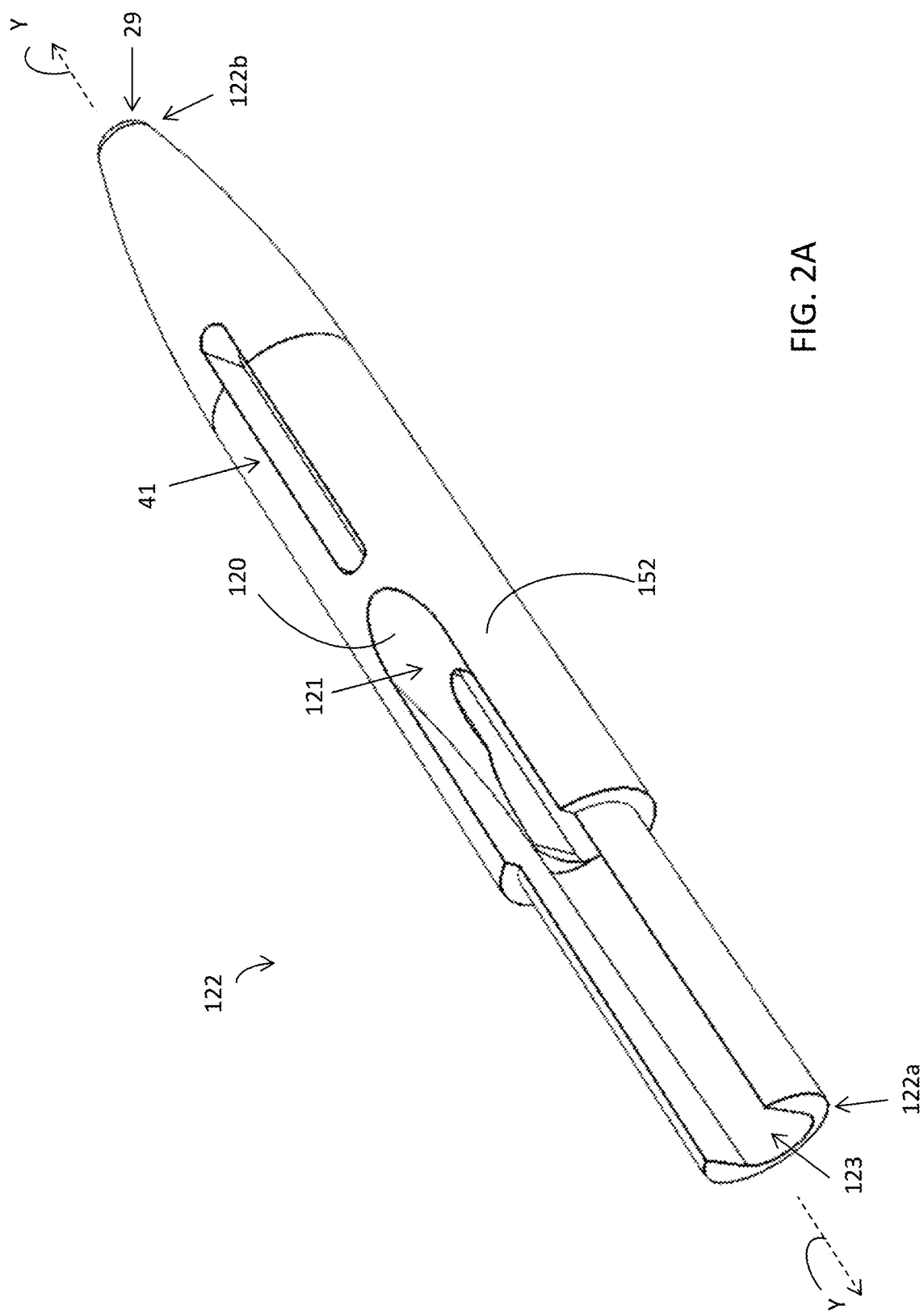
FIG. 2A is an isolated, magnified, top perspective view of a distal tip of another catheter system embodiment.
Figure 2B:
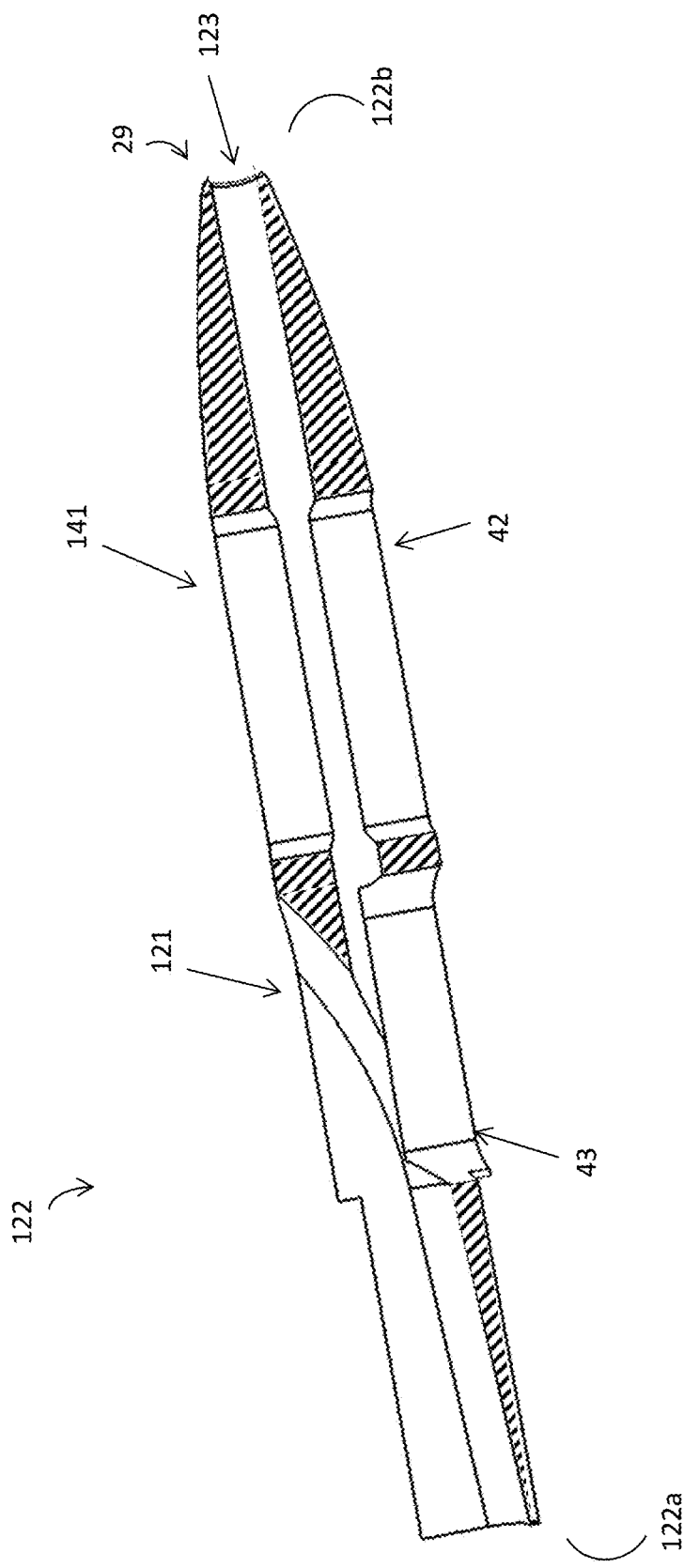
FIG. 2B is an isolated, cross-sectional view of the distal tip of the embodiment shown in FIG. 2A.
Figure 2C:
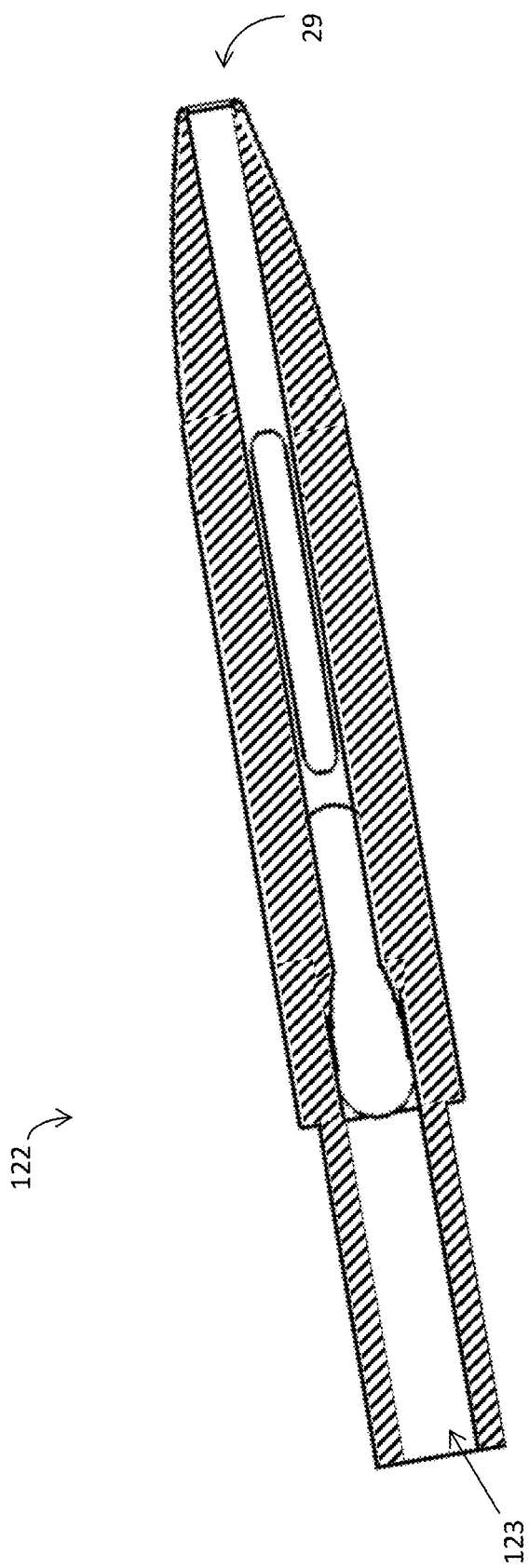
FIG. 2C is an isolated, cross-sectional view of the distal tip of the embodiment shown in FIG. 2A where the cross-section is taken on a plane that is transverse to that of FIG. 2B.

Referring to FIGS. 2A to 2C, another embodiment of the catheter system can comprise a distal tip 122 instead of distal tip 22. Distal tip 122 in the embodiment shown is the same as distal tip 22 except that a distal portion of sidewall 152 defines a curved ramp 120 configured to guide distal end 34a through side aperture 121. A portion of sidewall 152 opposite and proximal to aperture 121 can also be sloped or ramping. The angle of the slope can align with entrance angle of ramp 120. Lumen 123 is effectively a gap between the sloping surfaces, ramp 120 and the sloping sidewall 152. This gap is sized to accommodate needle wire 32. This gap can further be sized so that it does not accommodate catheter 34. In some embodiments, distal tip 22 comprises a concave, straight-sided channel or groove in sidewall that gradually increases in depth in a distal to proximal direction, where the surface of channel defines side aperture 21. This embodiment may be used with a catheter 34 with or without a curved section 34b.

In some embodiments, distal tip 122 comprises a channel that extends from proximal end 122a to an intermediate location between proximal end 122a and distal end 122b. The channel gradually decreases in depth in a proximal-to-distal direction. The base of the channel is curved along its length. Lumen 123 is in fluid communication with the channel. Proximal end 122a of distal tip 122 is configured to couple (e.g., mate) with distal end 18b of shaft 18.

Distal tip can further comprise a second side aperture 43 opposite the side aperture 21 such that a line transverse to longitudinal axis passes through both apertures 21 and/or 43.

Figure 3B:
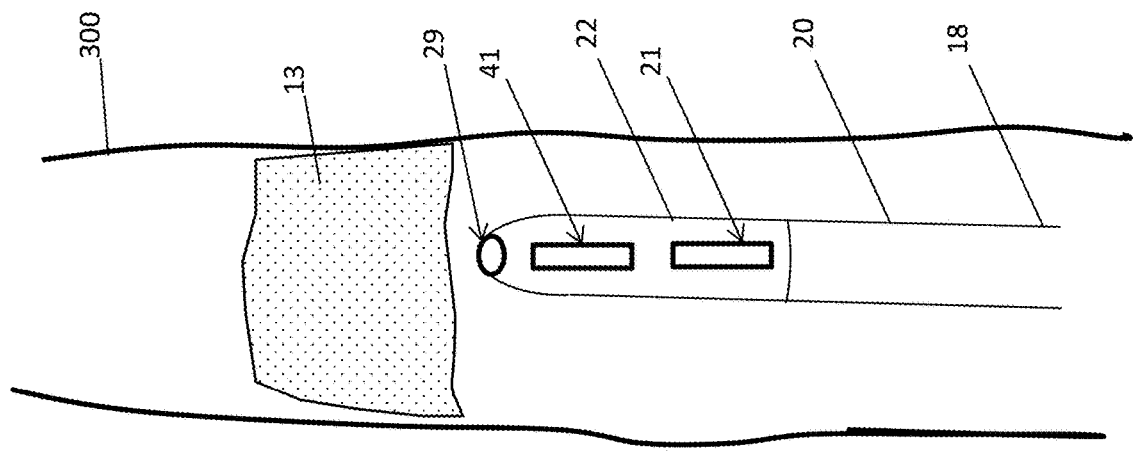

FIGS. 3A to 3I illustrate one embodiment of the present methods. Such methods can be performed using catheter systems described herein, but it is understood that the present methods can be performed using any suitable catheter system. FIG. 3A shows a patient 10 with an occlusion 13 involving a vessel 300 in neck region above the level of the superior vena cava (SVC) and the right atrium near reference numeral 15. As shown, a distal tip 22 of catheter 20 has approached occlusion 13. FIGS. 3B-3H are schematic illustrations of a series of process steps, the illustration showing vessel 300 with a vessel occlusion 13 and the distal portion of catheter system 12. FIG. 3I illustrates that the radiopaque target 30 placed on the surface of the patient 10 serves to set a desired exit site 40 on the skin of the patient and projection angle θ.

A method for gaining access to a vessel (e.g., a vein, central venous vein, right internal jugular, superior vena cava, or other suitable vessel) can comprise applying a radiopaque target 30 defining a radiolucent area 31 to the skin of the patient so that the radiolucent area defines a desired exit site 40 on the skin of the patient (FIG. 3A). Catheter system 12 can then be introduced into the patient in an area remote from exit site 40 (e.g., femoral vein) and advanced to a desired site in the vasculature (FIG. 3B). In the embodiment shown, the desired site is in the vicinity of occlusion 13. In some embodiments, an introducer catheter that has a lower stiffness than catheter 20 and/or catheter system 12 is first inserted into the vessel (e.g., femoral vein) and serves as a guide for catheter system 12.

To facilitate locating the occlusion relative to catheter system 12, a contrast agent can be injected into the vasculature and a radiographic instrument can be used to pin point the occlusion and the relative position of distal tip 22, which can comprise a radiopaque material. The introducer catheter can also have a radiopaque distal tip so that its location can be ascertained.

Once at the staging area, needle wire 32 can be advanced through the distal end aperture 29 of the catheter beyond distal end 22b and into occlusion 13 (FIG. 3C). In some embodiments, radiographic imaging can be used to determine the depth of penetration into the occlusion. The depth of penetration can depend on the extent of occlusion 13. Pommel 25 can be reciprocated as described above to advance needle wire 32. Since needle wire 32 is not curved like catheter 34, it will advance past side apertures (e.g., aperture 21, 401, and/or 42) and through distal end aperture 29. Needle wire 32 once inserted into the occlusion can define the path of catheter 20 such that when catheter 20 is advanced distally and pushed into the occlusion, it will follow the path of the needle wire.

Figure 3D:
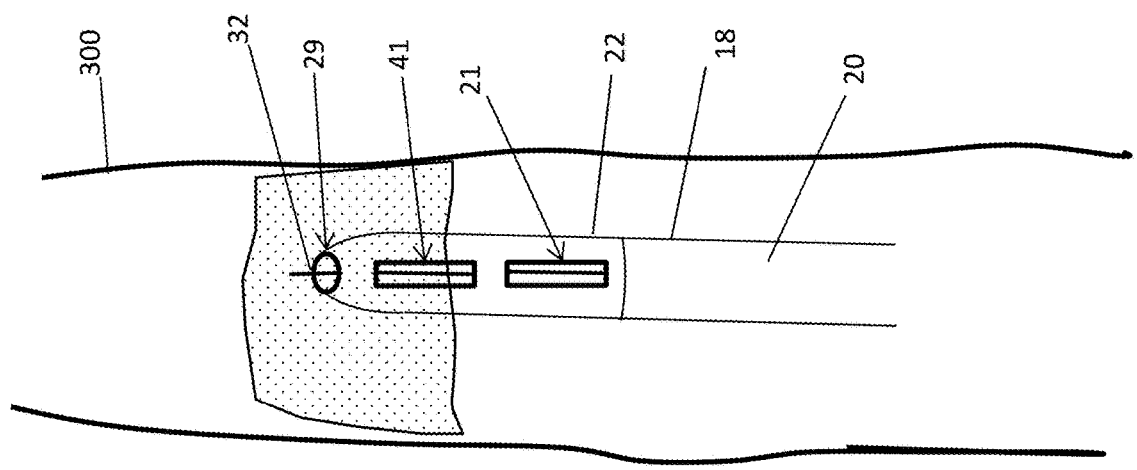

Once in position, catheter 20 is advanced over needle wire 32 and into occlusion 13 as well (FIG. 3D). Distal tip 22 can be pushed in to the occlusion by axial (along Y) and/or rotational forces (around Y) applied to handle 28 attached to the proximal end of catheter 20. In some embodiments, radiographic imaging can be used to determine the depth of penetration into occlusion 13. The depth of penetration can depend on the extent of occlusion 13.

To facilitate rotational alignment of the distal tip, distal tip 22 can be viewed using a radiographic instrument (such as an x-ray detector, e.g., CT-scanner, fluoroscope, ultrasound detector, or the like) through radiolucent area 31 of radiopaque target 30. Catheter 20 can be rotated so that side aperture is aligned with or faces radiolucent area 31 (FIG. 3E). The angle of the line extending between detector plane and distal tip 22 and to the longitudinal axis of patient or catheter (axis Y) can then be ascertained. Such angle substantially corresponds to the projection angle θ.

In some embodiments, the detector can be disposed on a C-arm. The angle of the C-arm relative to the patient can be used to determine the projection angle θ. Once the desired tip location is achieved, for example, the C-arm cranial angle is observed and it is used to determine the projection angle θ. In general, the C-arm is moved to image the tip 22 through the target 30. The angular location of distal tip 22 is determined by viewing side apertures 41 and/or 42 through target 30. FIG. 4 shows a schematic of the radiographic image. As tip 22 is rotated around its long axis the width and/or opacity of side apertures 41 and/or 42 varies and this changing image feature is used to determine the rotational orientation of distal tip 22.

FIG. 4 is a schematic view of a radiographic image that could be observed by a user. Distal tip 22 has side apertures 41 and/or 42 that can be view through the central aperture 31 of radiopaque target 30. The opacity of the apertures 41 and/or 42 can vary with the rotation of catheter 20. In general, apertures 41 and/or 42 will appear widest and/or brightest when one of aperture 41 and 42 is facing the central aperture 31. A user can advance or retract the tip 22 and rotate the distal tip 22 to optimize the exit path. Once the user has positioned the distal tip at the desired position and rotated it to the desired orientation, the projection angle θ can be ascertained from the C-arm. To set the projection angle θ, knob 16 is turned until the scale 17 corresponds to the desired projection angle. The angular range can vary between about 10 degrees to 90 degrees, e.g., 15 to 60 degrees as indicated on scale 17 or any other range between 10 to 90 degrees. The adjustability of the tip combined with the use of fluoroscopic imaging allows a user to precisely position and aim the distal end of the needle wire. This ability to view and direct the needle wire enhances patient safety.

Figure 3F:
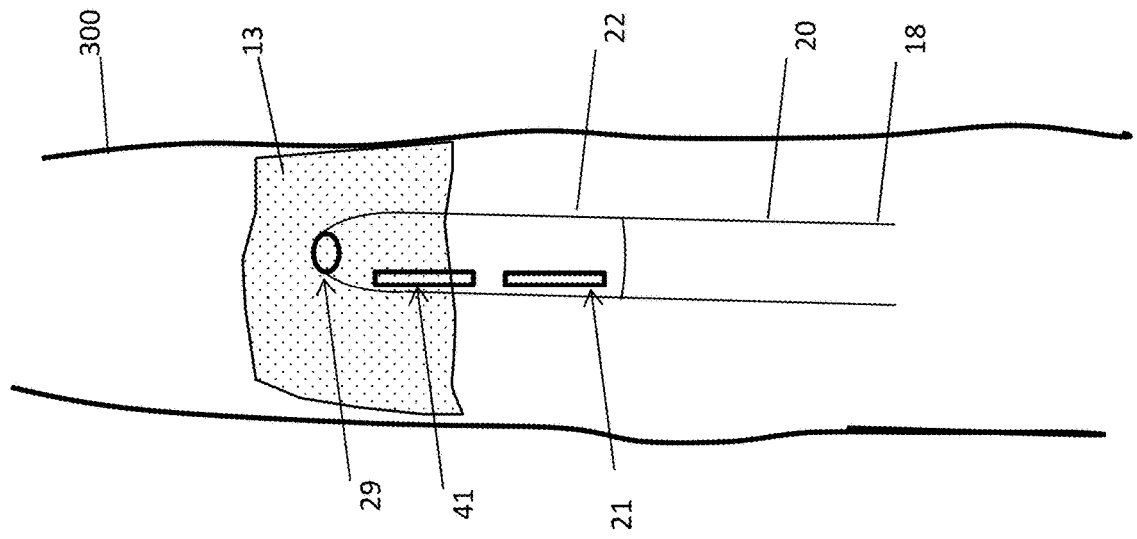

Needle wire 32 can then be retracted from beyond aperture 29 into catheter 20 and into catheter 34 (FIG. 3F). So as to not unduly effect the axial movement of catheter 34, the distal end of the needle wire is retracted so that its distal end is disposed in a non-curved portion of catheter 34 (e.g., not disposed in curved section 34b). In some embodiments, the distal end of needle wire 32 is spaced apart from distal end 34a of the catheter 34 at least a distance that is not impeding the curvature of catheter curved section 34b, e.g., a distance of 2 mm, 3 mm, 4 mm, 5 mm, 6 mm, 7 mm, 8 mm, 9 mm, 10 mm, or more.

Figure 3G:
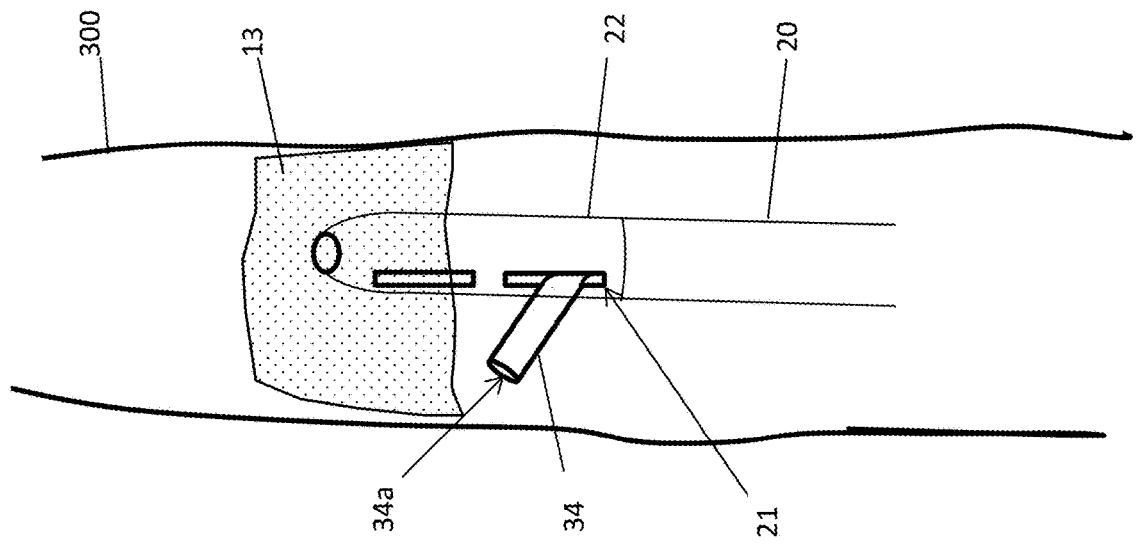
Figure 31:
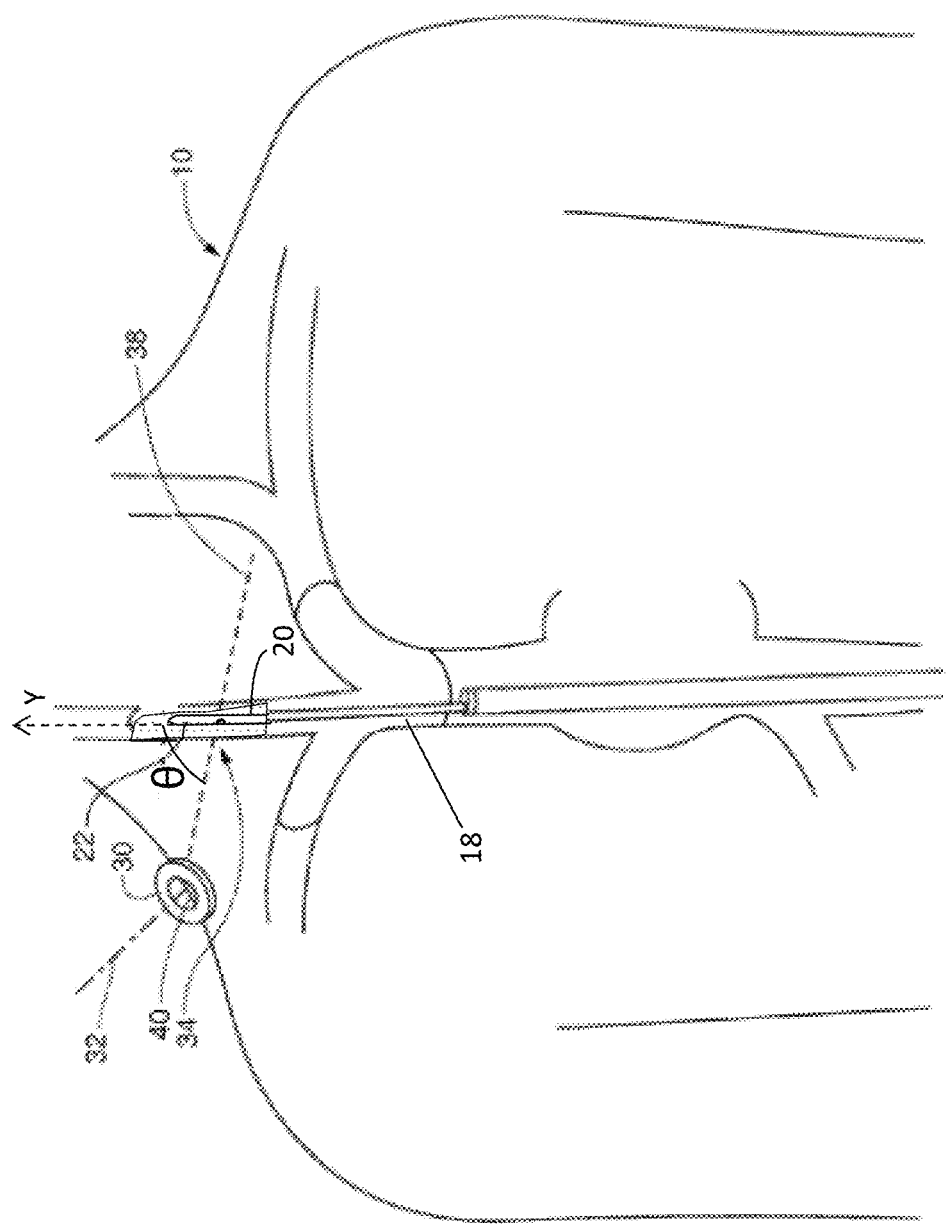

Catheter 34 can then be advanced a selected distance such that it extends from side aperture at the desired projection angle (FIG. 3G). Scale 17 can be used to ascertain the projection angle. Catheter 34 positioned at the desired projection angle is aimed at radiolucent area 31. Once catheter 34 is in position, needle wire 32 can be advanced through catheter 34 and into tissue, eventually through the skin of the patient adjacent the radiolucent area of the radiopaque target (FIGS. 3H and 3I). Distal end 32a of needle wire 32 can then be exteriorized to the patient.

With the needle wire 32 exteriorized as seen in the figure the access provided to the end of the wire allows additional intervention at the exit wound site as described below. For example, a dilation catheter can be coupled to the exteriorized needle wire and the dilation catheter can be drawn into the exit site by pulling on a proximal end of needle wire 32 thereby forming a dilated tissue track. A guide wire can be inserted into the dilation catheter and a medical device can be advanced over the guide wire along the dilated tissue track and into the vessel.

It should be understood that the foregoing device is broadly usable to establish an access point to a patient's vasculature from the inside out at any desired location. Once the access point has been established, it can be used for any desired medical procedure. For example, pacing leads for pacemakers can be delivered into a vessel after the tissue track has been established, and treatment devices (such as steerable catheters) can be delivered to the vessel through the access point.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown can include some or all of the features of the depicted embodiment. For example, elements can be omitted or combined as a unitary structure, and/or connections can be substituted. Further, where appropriate, aspects of any of the examples described above can be combined with aspects of any of the other examples described to form further examples having comparable or different properties and/or functions, and addressing the same or different problems. Similarly, it will be understood that the benefits and advantages described above can relate to one embodiment or can relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for providing access to a central venous system of a patient comprising:
   applying a radiopaque target having a radiopaque area and a radiolucent area to the skin of the patient so that the radiolucent area defines an exit area on the skin of the patient;
   introducing a catheter and a projection angle catheter into the patient in an area remote from the exit point, wherein the projection angle catheter is configured to extend out a side aperture of a distal tip of the catheter at a projection angle, and a needle wire is configured to extend through the projection angle catheter, wherein the catheter has a aperture at a distal end of the distal tip configured such that the needle wire can extend through the aperture, and wherein the needle wire is configured such that it can penetrate a muscle tissue or thrombus without deflection;

advancing the needle wire through the distal end aperture of the catheter into a thrombus in the central venous system;

advancing the distal tip of the catheter over the needle wire into the thrombus in the central venous system, wherein the side aperture of the distal tip is disposed out of the thrombus;

viewing the catheter and said distal tip under fluoroscopy through the radiolucent area of the radiopaque target;

rotating the catheter so that the side aperture and therefore the projection angle plane is aligned with the radiolucent area of the radiopaque target;

adjusting the projection angle catheter so that the projection angle is aimed at the radiolucent area of the radiopaque target; and advancing the needle wire through the projection angle catheter when the distal tip of the catheter is disposed in the thrombus and the side aperture of the distal tip is disposed out of the thrombus, such that the distal end of the needle wire advances at an angle relative to the catheter and penetrates the skin of the patient adjacent the radiolucent area of the radiopaque target thereby providing a distal end of the needle wire exterior to the skin.

2. The method of claim 1, further comprising retracting the needle wire from the thrombus into the catheter.

3. The method of claim 1, wherein the projection angle catheter comprises a preformed curved distal portion.

4. The method of claim 3, further comprising retracting the needle wire from beyond the distal end aperture into the catheter and into the projection angle catheter, wherein the distal end of the needle wire is spaced apart from a distal end of the projection angle catheter at least a distance such that the needle wire is not impeding the curvature of the distal portion.

5. The method of claim 3, further comprising retracting the needle wire from beyond the distal end aperture into the catheter and into the projection angle catheter, wherein the distal end of the needle wire is disposed in a non-curved portion of the projection angle catheter.

6. The method of claim 1, further comprising retracting the needle wire from beyond the distal end aperture into the catheter and into the projection angle catheter, wherein the distal end of the needle wire is spaced apart from a distal end of the projection angle catheter at least a distance of 3 mm.

7. The method of claim 1, further comprising:

attaching a dilation catheter to the exteriorized needle wire and drawing the dilation catheter into the exit point by pulling on a proximal end of the needle wire thereby forming a dilated tissue track.

8. The method of claim 7, further comprising: advancing a guide wire into the dilation catheter and advancing a medical device over the guide wire along the dilated tissue track into the central venous system.

9. The method of claim 1, wherein the introducing step occurs through a guide catheter.

10. The method of claim 1, wherein the catheter is configured such that the distal tip can penetrate a thrombus without deflection.

11. A method for providing access to a central venous system of a patient comprising:

introducing a catheter into the patient, wherein the catheter has a projection angle catheter configured to extend out a side aperture of a distal tip of the catheter at a projection angle, and a needle wire configured to extend through the projection angle catheter, wherein the catheter has an aperture at a distal end of the distal tip configured such that the needle wire can extend through the aperture in a direction substantially parallel with a longitudinal axis of the catheter, wherein the projection angle is angled with respect to the longitudinal axis;

advancing the needle wire through the distal end aperture of the catheter and into a vessel occlusion, wherein the needle wire is configured such that it can penetrate a muscle tissue or vessel occlusion without deflection;

advancing the distal tip of the catheter over the needle wire into the vessel occlusion, wherein the aperture at the distal end of the distal tip is disposed out of the vessel occlusion;

retracting the needle wire into the catheter and the projection angle catheter;

advancing the projection angle catheter so that the catheter extends through the side aperture; and advancing the needle wire through the projection angle catheter and through the skin of the patient when the distal tip of the catheter is disposed in the vessel occlusion and the side aperture of the distal tip is disposed out of the vessel occlusion, thereby providing a distal end of the needle wire exterior to the skin.

12. The method of claim 11, wherein the vessel occlusion is located within the central venous system.

13. The method of claim 11, wherein the needle wire follows a substantially straight path when advanced from the catheter to the surface of the skin.

* * * * *

UNITED STATES PATENT AND TRADEMARK OFFICE
CERTIFICATE OF CORRECTION

| | |
|---|---|
| PATENT NO. | : 11,801,065 B2 |
| APPLICATION NO. | : 17/089551 |
| DATED | : October 31, 2023 |
| INVENTOR(S) | : John Gurley |

It is certified that error appears in the above-identified patent and that said Letters Patent is hereby corrected as shown below:

On the Title Page

Item (22) reads, "Filed: May 24, 2023", and should read, "Filed: November 4, 2020"

Signed and Sealed this
Second Day of January, 2024

*Katherine Kelly Vidal*

Katherine Kelly Vidal
*Director of the United States Patent and Trademark Office*